United States Patent [19]
Holmes

[11] Patent Number: 5,836,937
[45] Date of Patent: Nov. 17, 1998

[54] ROD CUTTER WITH DEPTH GAUGE

[76] Inventor: Russell P. Holmes, 201 Newbury St., Apt. #405, Boston, Mass. 02116

[21] Appl. No.: 922,717

[22] Filed: Sep. 2, 1997

[51] Int. Cl.⁶ .................................................. A61B 17/00
[52] U.S. Cl. .................................. 606/1; 606/172; 30/179
[58] Field of Search ............................... 606/1, 174, 172, 606/207; 30/179, 233

[56] References Cited

U.S. PATENT DOCUMENTS

| | | | |
|---|---|---|---|
| 1,042,901 | 10/1912 | Fletcher | 30/179 |
| 5,290,299 | 3/1994 | Fain et al. | 606/1 |
| 5,364,397 | 11/1994 | Hayes et al. | 606/1 |

*Primary Examiner*—Michael Powell Buiz
*Assistant Examiner*—Kevin Truong
*Attorney, Agent, or Firm*—Cesari and McKenna, LLP

[57] ABSTRACT

A rod cutting instrument having a depth gauge and/or a anti-twisting strap is provided. The depth gauge is secured to the strap of a set of surgical cutting jaws. The gauge has a U-shaped guide at one end thereof which extends into the cutting area defined by the cutting blades of the jaws. The guide is sized to encompass a surgically-implanted rod which is to be severed. The depth gauge is dimensioned so that when it is placed against the rod, it provides sufficient blade depth such that the blades can cut the rod all the way through. The depth gauge may include two guide sizes or depths, one on either end of the guide, which can be selected depending upon the size of rod to be cut and removed, or for cutting rods outside of the body. The anti-twisting strap is attached to an opposite side of the rod cutter. The anti-twisting strap includes a strap portion that controls the movement of the jaws and a stabilizing unit that incorporates two legs, which extend along the cutting blades to resist against attempts by a surgeon to twist the handles and potentially break the blades.

8 Claims, 5 Drawing Sheets

ROD CUTTER WITH DEPTH GAUGE

FIELD OF THE INVENTION

This invention relates generally to improvements in surgical instruments used for cutting surgical components, such as rods and the like, and particularly, for cutting and removal of rods that have been implanted adjacent to the spine to enhance spinal strength or for straightening of the spine.

BACKGROUND OF THE INVENTION

In certain medical circumstances, it is necessary to place a mechanical device, such as a Harrington rod, adjacent to the spine. This is to promote the natural healing of the spine in a straight spatial disposition, or to enhance straightening of the spine in cases of disease such as scoliosis. In some surgical procedures, chips of bone which have been removed from another portion of the body, such as the hip, are placed in proximity to the healing spinal site. These chips act as mortar to promote bone fusion.

Under various circumstances, the surgical rods must be cut. For example, a rod being used by a surgeon may be longer than necessary for the site in which it is to be used, so the excess rod is to be cut off. In other cases, the rod is to be removed from the body in which case it is first cut in situ into pieces. For example, after spinal bone fusion and/or the desired straightening is achieved, the implanted rod may be surgically removed from the body. In other cases, the desired healing is not being achieved, so the rod needs to be removed from the patient. In order to remove the rod, a surgeon first cuts the rod into smaller, more easily extractable, pieces. To do this in situ, the surgeon surgically inserts a rod cutter through an appropriate incision in the proximity of the rod, and thus, the spine. In order to promote recovery, the incision is made as small as possible, while still accommodating the rod cutter. Additionally, bone may have grown around the rod and must be cleared away. Ideally, only a small amount of bone is removed. This leaves the surgeon with minimal working space and a somewhat restricted view of the rod. Positioning the rod cutter in various locations along the rod, the surgeon severs the rod into the desired pieces. The rod pieces are then extracted using a suitable instrument. Rod cutters for this purpose have been known and described. However, problems have been encountered with such rod cutters.

Due to the location of the rod adjacent to the spinal cord, the surgical procedures associated with removal of the rod can be difficult due both to the lack of space and the risk of damage to the surrounding area. In addition, bone may have fused around the rod, and a portion of such bone must be removed, further complicating the procedure. More specifically, once the rod cutters are inserted into the body and placed around the rod for severing, the surgeon's view of the site is partially blocked by both the cutter and the surrounding bone. Thus, the surgeon may not be able to visably check the depth of the cutter blades to assure that the blades are positioned about the rod to cut all the way through the rod. In addition, the rod cutter may be prevented from going deep enough around the rod due to bone on the distal side of the rod not having been adequately cleared away.

If the blades do not cut clear through the rod, a small edge portion of the rod may remain connected after the rod cutter is operated. To completely sever the rod, a surgeon then typically twists the rod cutters in an attempt to snap the remaining connected rod piece in half. This often results in cutter blade breakage and possible loss of the blade in situ. It may also result in injury to the surrounding area.

Alternatively, the surgeon may have unknowingly pushed the blades too far past the rod, and the blades may cut into nearby bone, nerve and/or surrounding tissue.

In other instances, rods are cut outside the body for sizing or other purposes. In such cases, the depth of the rod in the cutting area between the open blades is not as critical because the risks associated with in situ work are not present. It is desirable to have a rod cutter which is also provided with different cutting positions along the cutting blade for other types of procedures. Having several operative positions any one of which may be selected for a given procedure also reduces repeated use of the same physical location on the cutting blade, thus reducing jaw and blade fatigue.

Accordingly, it is an object of the present invention to provide improvements in rod cutting instruments, to provide for optimal severance of the rod while minimizing injury to the adjacent area.

It is another object of the invention to reduce the surgeon's ability to twist the handles and thereby to reduce the risk of blade breakage during surgical procedures.

Yet another object of the invention is to provide an attachment for existing instruments which can be readily adapted to such instruments for immediate use in surgical procedures.

SUMMARY OF THE INVENTION

The rod cutting instrument of the present invention includes a depth gauge that includes at one end a U-shaped guide that extends into the cutting area defined by the cutting blades of the rod cutter jaws. The U-shaped guide, which is contoured to the diameter of a rod to be cut, receives the rod and positions the rod cutter blades relative to the rod such that the blades will cut all the way through the rod. The guide also prevents the blades from extending too far past the rod, and thus, prevents the blades from cutting into nearby bone and/or tissue.

The depth gauge attaches to a conventional strap that essentially limits the opening of the rod cutter jaws. Accordingly, the depth gauge can be readily incorporated into existing rod cutter designs.

The depth gauge may further include at a second end a second U-shaped guide that is contoured differently than the first guide. Preferably, the depth of the second guide will be greater than that of the first guide to accommodate non-in situ cutting, or for use in cutting rods of a different dimension. The gauge may then be removably attached to the strap, so that the appropriate guide can be selected to accommodate use in particular procedures.

Another feature of the invention is an anti-twisting strap that replaces the conventional strap on an opposite side of the rod cutter. The anti-twisting strap performs two functions, namely, it includes a conventional strap portion that controls the movement of the jaws, and it incorporates a stabilizing unit that extends along a portion of the rod cutter blades, to provide stability to the blades when a torsional or twisting force is applied to the blades; in addition, the stabilizing unit comes in contact with the rod, thus, reducing the doctor's ability to twist the handles.

The stabilizing unit has two legs that join to form a U-shaped indentation. The legs are oriented to extend partially along the cutting blades, when the blades are engaging a rod. The legs essentially prevent the blades from bending or twisting in response to torsional forces applied in the blades by a twisting of the rod cutter to, for example, complete a cut. The depth gauge guide also works in tandem with the anti-twisting strap to further reduce the effects of twisting.

To ensure that the anti-twisting strap does not interfere with the operations of the depth gauge, the U-shaped indentation in the stabilizing unit has dimensions that are preferably larger, but at least as large, as those of the depth gauge guides. The depth of this indentation also allows for the rod cutter to be used in the alternative position for non-in situ cutting which is desirable as described herein. The depth gauge and the anti-twisting strap can be installed on an otherwise conventional rod cutter, with minimal increases to the size and weight of the cutter. The two devices do not substantially alter the size of the rod cutter cutting area or the jaws, and thus, a rod cutter that includes the depth gauge and/or the anti-twisting strap has conventional dimensions.

BRIEF DESCRIPTION OF THE DRAWINGS

The foregoing discussion will be understood more readily from the following detailed description of the invention when taken in conjunction with the accompanying drawings, in which.

DETAILED DESCRIPTION OF THE PREFERRED EMBODIMENTS

Figure 1:
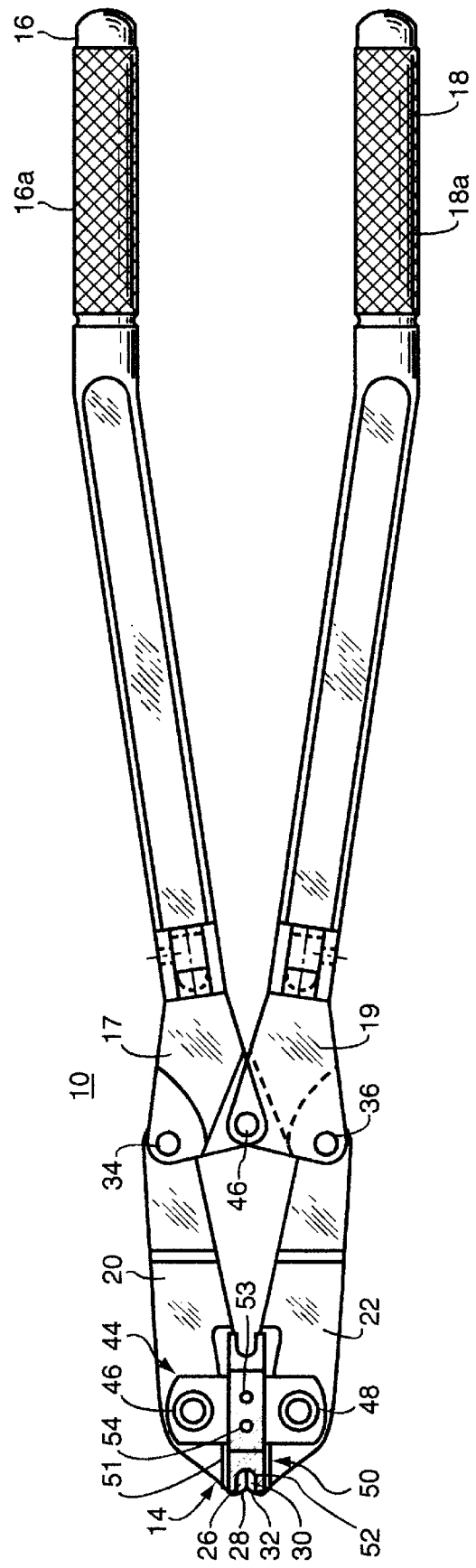
FIG. 1 is top plan view illustrating the basic components of the rod cutter with the rotatable depth gauge illustrated in conjunction with the strap of the rod.
Figure 3:
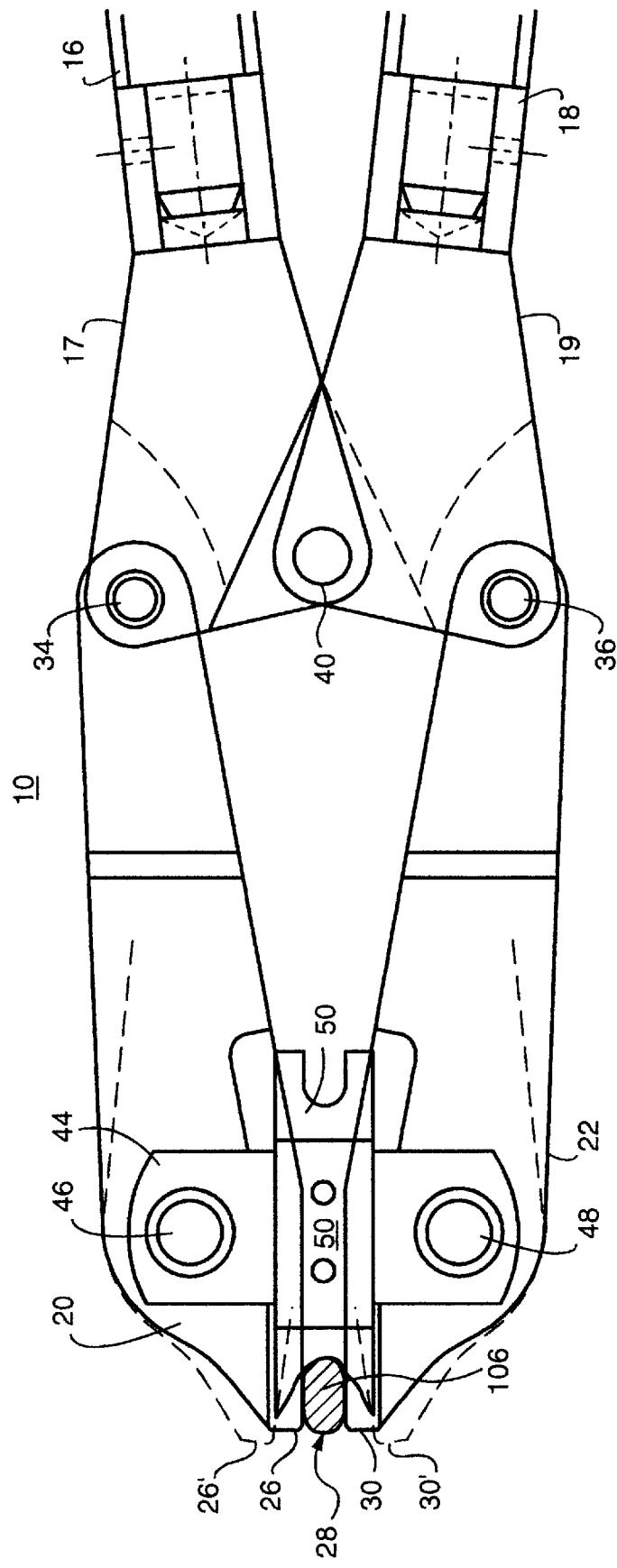
FIG. 3 is an isometric view of the rod cutter illustrating the depth gauge with OPEN position of the rod cutting blades shown in phantom.

FIG. 1 illustrates a rod cutter 10 which has a cutting end 14 and handles 16 and 18. The cutting end 14 has movable jaws 20 and 22. The jaw 20 is rotatably attached at pin 34 to a handle extension 17 of the handle 16, and the jaw 22 is rotatably attached at the pin 36 to a handle extension 19 of the handle 18. The handle extensions 17 and 19 are rotatably connected together at pin 40. When the handles 16 and 18 are rotated outwardly using grip portions 16a and 18a, respectively, jaws 20 and 22 are rotated about the various pins, to draw the blades 26 and 30 apart. The blades 26 and 30 then define a cutting area 28 (FIG. 3).

A strap 44 attaches to the jaws 20 and 22 and operates in a conventional manner to constrain the jaws from opening too widely. Fasteners 46 and 48 hold the strap 44 in place.

Figure 2A:
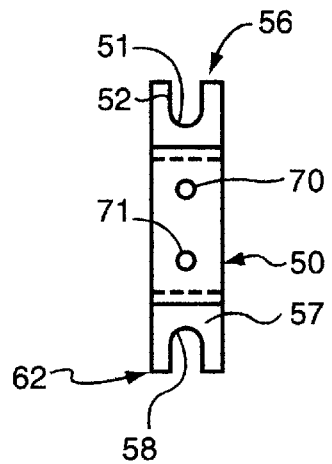
FIGS. 2A and 2B are top plan views illustrating the depth gauge and the strap to which it is attached, respectively.
Figure 2B:
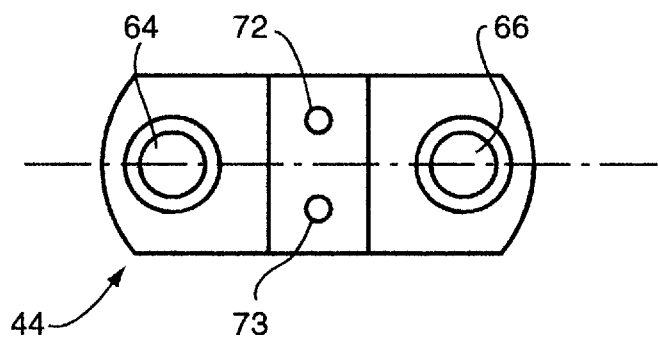

Referring also to FIGS. 2A–2B, a depth gauge 50 is attached to the strap 44 with pins 53 and 54. The depth gauge 50, which is oriented perpendicular to the strap 44, includes at one end 56 a U-shaped guide 51 that extends into the cutting area defined by the cutting blades. The guide 51 includes an indentation 52 that is dimensioned to the size of a rod (not shown) to be cut. As discussed below with reference to FIG. 3, the guide 51 receives a rod in the indentation 52. When the rod is held in the guide, the blades 26 and 30 are positioned about the rod to cut completely through the rod while cutting into surrounding bone and/or tissue only a minimal amount.

The depth gauge 50 is attached to the strap 44 by the pins 53 and 54 that extend through holes 70 and 71. The holes align with holes 72 and 73 in the strap 44. The strap 44 is installed on the jaws 20 and 22 by fasteners 46 and 48 that extend through holes 64 and 66.

The depth gauge 50 may include at a second end 62 a second guide 57 that has an indentation 58 which is of a different depth than the indentation 52 in the guide 51. This second guide 57 can be used with smaller or larger diameter rods, or to allow the rod cutter to be used outside the body. The two-ended depth gauge may be removably attached to the strap 44, such that the gauge 50 can be re-oriented to position the appropriate guide 51 or 57 within the cutting area 28 (FIG. 3). It is preferred, however, that the depth gauge 50 is permanently attached to the strap, to avoid the inconvenience of loose parts. For a particular procedure the surgeon then selects the rod cutter that has installed thereon the depth gauge that is oriented to position within the cutting area the guide 51 or 57 that is sized to the rod to be surgically removed.

The operation of the depth gauge 50 can be better understood with reference to FIG. 3. To perform a cutting operation, a surgeon manipulates the handles 16 and 18 of the rod cutter 10 to separate the blades 26 and 30. The handle extensions 17 and 19 rotate about pin 40. The jaw 20 rotates, in turn, about pin 34, which causes the blade 26 to move to an OPEN position 26' as shown in phantom in FIG. 3. Similarly, the jaw 22 rotates about pin 36, which causes the blade 30 to move to an OPEN position 30' as shown in phantom. This OPEN position allows the blades to engage the entirety of the diameter of a rod 106.

The surgeon drives the rod cutter 10 toward the rod with the blades 26 and 30 extending on opposite sides of the rod 106. The guide 51 of the depth gauge 50 receives the rod 106, and stops the progress of the blades 26 and 30 past the rod. The guide 51 thus prevents the surgeon from driving the blades 26 and 30 too far past the rod. With the rod 106 held in the guide, the blades 26 and 30 extend just far enough to cut through the rod 106. The surgeon then manipulates the handles 16 and 17 to cut clean through the rod with the blades 26 and 30.

Figure 4:
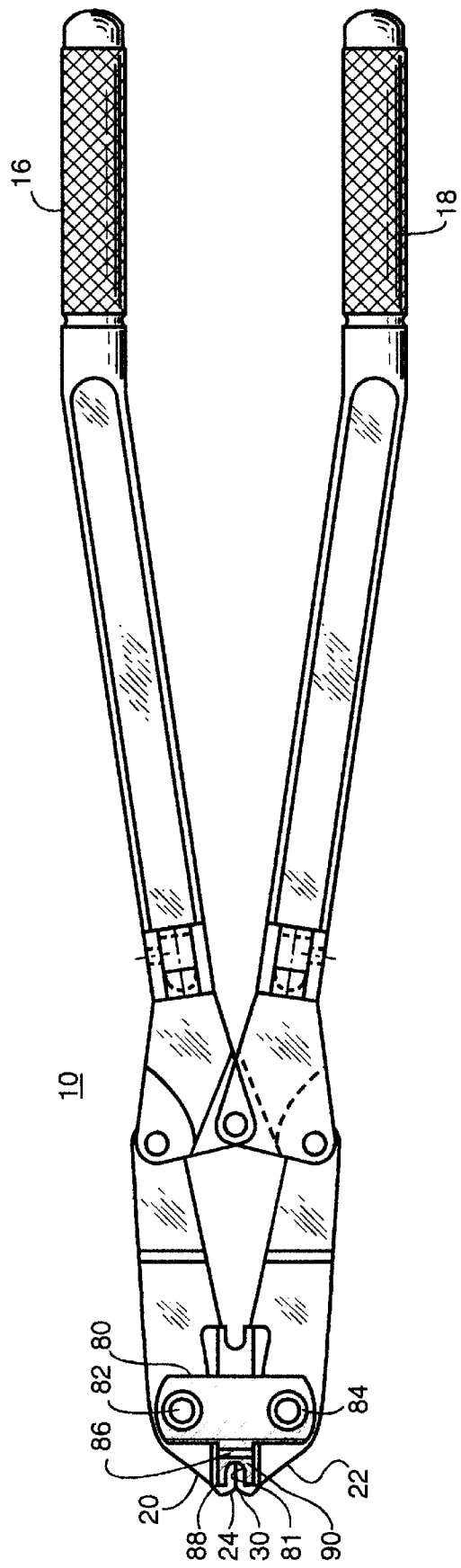
FIG. 4 is a bottom plan view of the rod cutter illustrating the stabilizing unit.

FIG. 4 illustrates a anti-twisting strap 80, which replaces the conventional strap on an opposite side of the rod cutter 10 from the depth gauge 50. The anti-twisting strap 80 includes a U-shaped stabilizing unit 86, with legs 88 and 90 that extend along the jaws 20 and 22. The legs 88 and 90 provide support to the blades 26 and 30 against torsional forces that develop therein if the rod cutter 10 is twisted during a cutting operation.

A cutout 81 formed between the legs 88 and 90 is dimensioned such that it does not interfere with the rod cutting operations. The cutout 81 must be at least as large and is preferably larger than the indentations 52 or 58 in the guides 51 and 57 of the depth gauge 50. This ensures that the depth gauge 50, and not the stabilizing unit, controls the position of the blades 26 and 30 relative to the rod 106.

Figure 5:
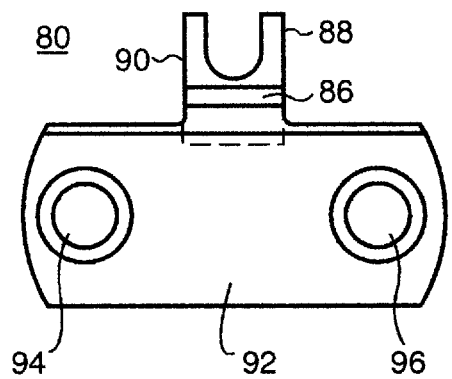
FIG. 5 is a top plan view of the stabilizing unit of FIG. 4.

The anti-twisting strap 80 is shown in greater detail in FIG. 5. The strap 80 has holes 94 and 96 through which suitable fasteners (not shown) can be passed for attachment to the jaws 20 and 22 (FIG. 1) of the rod cutter 10. The strap 80 incorporates the stabilizing unit 86.

As the rod cutter 10 is being used to cut a rod, the legs 88 and 90 of the stabilizing unit 86 are adjacent to and, thus, support the cutting blades 26 and 30. As the surgeon manipulates the rod cutter 10 to cut through a rod, which rod can be relatively thick compared to the cutting blades, there may be a tendency for the rod cutter 10 to twist or rotate away from the plane of the slice. Such twisting and/or rotation can place stress on the cutter blades and may lead to blade breakage. In such cases, the legs 88 and 90 of the stabilizing unit 86 help to support the blades 26 and 30 against bending and maintain their alignment with the remainder of the jaws 20 and 22, respectively. The stabilizing unit 86 thus reduces the risk of blade breakage and the associated damage to the surrounding bone and tissue.

The anti-twisting strap may be used without the depth gauge 50 (FIG. 1), however, it is expected that the two will be used together as these components work together to promote optimal cutting performance.

It should be understood that the present invention provides a rod cutter assembly which provides a surgeon with a guide to facilitate fully severing a surgically-implanted rod during a procedure for removing the rod, or cutting of the rod for other purposes. The guide also ensures that the blades of the rod cutter will not be driven too far past the rod, and thus prevents injury to the surrounding bone and tissue. The guide is also useful in cutting rods outside of the body in that it allows for cutting at different locations along the blades thus reducing blade fatigue.

The present invention further provides a rod cutter with additional stability to reduce the risk of blade breakage during the procedure. The guide and strap of the present invention are also advantageous in that these components can be readily adapted to existing rod cutting instruments.

The terms and expressions employed herein are used as terms of description and not of limitation and there is no intention in the use of such terms and expression, of excluding any equivalents of the features shown and described or portions thereof, but it is recognized that various modifications are possible within the scope of the invention claimed.

What is claimed is:

1. A surgical cutting instrument for severing a rod-shaped surgically-implanted component in situ, the cutting instrument including:
   (A) a set of jaws rotatably connected together at one end such that said jaws are capable of opening and closing in a scissor-like manner, each jaw in said set having a cutting blade on one edge thereof which opposes the cutting edge of the other jaw, the cutting blades defining a cutting area when in an open position;
   (B) a strap means attached across said jaws and displaced from the end of said jaws such that said strap restricts said jaws from opening more than a predetermined distance;
   (C) depth gauge means attached to said strap means, said depth gauge means having
      i) a body portion for securing said depth gauge means to said strap, and
      (ii) a first U-shaped guide attached to one end of said body portion and extending into said cutting area, said U-shaped guide being dimensioned to receive said rod-shaped component, the depth gauge being held by said strap to position the first U-shaped guide within said cutting area, the first U-shaped guide holding the rod such that said cutting blades extend sufficiently past the rod-shaped component to sever the component.

2. The surgical cutting instrument of claim 1 further including
   a second U-shaped guide portion being disposed at the opposite end of said body portion from said first U-shaped guide, said second guide being of a different dimension than said first U-shaped guide, and
   said body portion being removably attached to said strap means in such a manner that one of said first and second U-shaped guides can be selected for positioning within said cutting area.

3. The surgical cutting instrument of claim 1 further comprising an anti-twisting strap secured to said jaws on a side opposite to that upon which said depth gauge is disposed, said anti-twisting strap including a stabilizing unit with legs that extend, respectively, along the cutting blades to support the cutting blades against bending and twisting in response to torsional forces.

4. The surgical cutting instrument of claim 3 wherein said legs define a U-shaped indentation that has dimensions that are at least as large as the dimensions of said first and second U-shaped guides.

5. The surgical cutting instrument of claim 4 further including
   a second U-shaped guide portion being disposed at the opposite end of said body portion from said first U-shaped guide, said second guide being dimensioned to receive a rod-shaped component of another size, and
   said body portion being removably attached to said strap means in such a manner that one of said first and second U-shaped guides can be selected for positioning within said cutting area.

6. A surgical cutting instrument for severing a rod-shaped surgically-implanted component in situ, the cutting instrument including:
   (A) a set of jaws rotatably connected together at one end such that said jaws are capable of opening and closing in a scissor-like manner, each jaw in said set having a cutting blade on one edge thereof which opposes the cutting edge of the other jaw, the cutting blades defining a cutting area when in an open position;
   (B) a strap attached across said jaws and displaced from the end of said jaws such that said strap means restricts said jaws from opening more than a predetermined distance;
   (C) depth gauge means attached to said strap means, said depth gauge means having
      i) a body portion for securing said depth gauge means to said strap, and
      (ii) a first U-shaped guide attached to one end of said body portion and extending into said cutting area, said U-shaped guide being dimensioned to receive said rod-shaped component, the depth gauge being held by said strap to position the first U-shaped guide within said cutting area, the first U-shaped guide holding the rod such that said cutting blades extend sufficiently past the rod-shaped component to sever the component; and
   D) an anti-twisting strap secured to said jaws on a side opposite to that upon which said depth gauge is disposed, said anti-twisting strap including a stabilizing unit with legs that extend, respectively, along said cutting blades to strengthen the cutting blades against bending and twisting in response to torsional forces.

7. The surgical cutting instrument of claim 6 wherein said legs define a U-shaped indentation that has dimensions that are at least as large as the dimensions of said first and second U-shaped guides.

8. The surgical cutting instrument of claim 6 further including
   a second U-shaped guide portion being disposed at the opposite end of said body portion from said first U-shaped guide, said second guide being dimensioned to receive a rod-shaped component of another size, and
   said body portion being removably attached to said strap means in such a manner that one of said first and second U-shaped guides can be selected for positioning within said cutting area.

* * * * *